(12) United States Patent
Knebel

(10) Patent No.: US 8,300,310 B2
(45) Date of Patent: Oct. 30, 2012

(54) METHOD FOR FCS MEASUREMENTS

(75) Inventor: Werner Knebel, Kronau (DE)

(73) Assignee: Leica Microsytems CMS GmbH, Wetzlar (DE)

(*) Notice: Subject to any disclaimer, the term of this patent is extended or adjusted under 35 U.S.C. 154(b) by 0 days.

(21) Appl. No.: 13/210,554

(22) Filed: Aug. 16, 2011

(65) Prior Publication Data

US 2011/0299156 A1 Dec. 8, 2011

Related U.S. Application Data

(63) Continuation of application No. 12/088,639, filed as application No. PCT/EP2006/066861 on Sep. 28, 2006.

(30) Foreign Application Priority Data

Sep. 29, 2005 (DE) .......................... 10 2005 046 510

(51) Int. Cl.
*G02B 21/06* (2006.01)
*G01J 3/30* (2006.01)

(52) U.S. Cl. ........................................ 359/389; 356/318
(58) Field of Classification Search ................ 359/385, 359/389; 356/317, 318
See application file for complete search history.

(56) References Cited

U.S. PATENT DOCUMENTS

| | | |
|---|---|---|
| 6,094,300 A | 7/2000 | Kashima et al. |
| 6,693,742 B1 | 2/2004 | Winterot et al. |
| 2002/0121610 A1 | 9/2002 | Tewes et al. |
| 2003/0071227 A1 | 4/2003 | Wolleschensky |
| 2003/0197924 A1 | 10/2003 | Nakata |
| 2004/0257562 A1 | 12/2004 | Wachsmuth |
| 2006/0250690 A1 | 11/2006 | Ulrich et al. |
| 2007/0109536 A1 | 5/2007 | Weiss et al. |
| 2007/0152556 A1 | 7/2007 | Bohm et al. |

FOREIGN PATENT DOCUMENTS

| | | |
|---|---|---|
| DE | 19702753 A1 | 7/1998 |
| DE | 19951482 A1 | 5/2001 |
| EP | 0941470 B1 | 9/1999 |
| JP | 6160724 A | 6/1994 |
| WO | WO 9823944 A1 | 6/1998 |
| WO | WO 2005031428 A1 | 4/2005 |
| WO | WO 2005054924 A1 | 6/2005 |

*Primary Examiner* — Alessandro Amari
(74) *Attorney, Agent, or Firm* — Leydig, Voit & Mayer, Ltd.

(57) ABSTRACT

A method for conducting FCS measurements includes providing a sample volume, emitting a target light having a first wavelength from a target light source, and marking an FCS volume in the sample volume with the target light by directing the target light onto the sample volume. An illuminating light having a second wavelength is emitted from an illuminating light source, the second wavelength being different than the first wavelength, and the illuminating light is directed onto the sample volume.

10 Claims, 2 Drawing Sheets

METHOD FOR FCS MEASUREMENTS

CROSS REFERENCE TO PRIOR APPLICATIONS

This patent application is a continuation of copending U.S. patent application Ser. No. 12/088,639, filed Mar. 28, 2008, which is a U.S. national phase application under 35 U.S.C. §371 of International Patent Application No. PCT/EP2006/066861, filed Sep. 28, 2006, and claims benefit of German Patent Application No. 10 2005 046 510.2, filed Sep. 29, 2005, all three of which are hereby incorporated by reference in their entirety herein. The International Application was published in German on Apr. 5, 2007 as WO 2007/036559 A1 under PCT Article 21(2).

FIELD

The invention relates to a microscope system for Fluorescence Correlation Spectroscopy (FCS) measurements, and in particular, to a microscope system for conducting FCS measurements.

BACKGROUND

European Patent EP 0 941 470 describes a fluorescence correlation spectroscopy module for a microscope. The FCS module can additionally be connected to a microscope of any desired design. Fluorescence correlation spectroscopy allows the investigation of molecular dynamic processes to be studied. For this purpose, the particles contained in solution are doped with fluorescent dyes, and these dyes are then excited by light of a particular wavelength. The excitation light coming from a laser is coupled into the module via a flange joint for an optical waveguide. In the FCS module known from prior art, it is difficult to align the FCS detection volume with the sample area, which is to be investigated.

SUMMARY

The present invention provides a method of conducting FCS measurements. The method includes providing a sample volume, emitting a target light having a first wavelength from a target light source, and marking an FCS volume in the sample volume with the target light by directing the target light onto the sample volume. An illuminating light having a second wavelength is emitted from an illuminating light source, the second wavelength being different than the first wavelength, and the illuminating light is directed onto the sample volume.

BRIEF DESCRIPTION OF THE DRAWINGS

In the drawings, the subject matter of the invention is illustrated schematically, and will be described in the following with the aid of the figures, in which.

DETAILED DESCRIPTION

The present invention is directed to a microscope method which can be used to reliably perform the alignment with the sample volume to be investigated. This can be achieved by a microscope system comprising the features described below.

In accordance with one embodiment of the invention the microscope system for conducting Fluorescence Correlation Spectroscopy (FCS) measurements can be provided with a target light source for marking an FCS volume. Here, the light of the target light source can be also directed onto the sample volume via the plurality of optical elements. The wavelength of the first light source preferably differs from the wavelength of the target light source.

A combining element can be provided which combines the illuminating light of the first light source with the light of the target light source to form a common beam path. The light of the target light source preferably has a longer wavelength than the illuminating light of the first light source.

In accordance with a further aspect of the present invention, the light of the target light source can have a wavelength that is in the region of red light. In the same way, the light of the target light source can have a wavelength that is in the region of IR light. In the case of IR light, a camera is provided which registers the IR light and converts it into an image visible to the user. Furthermore, the target light source is preferably provided with a correcting optics in order to compensate chromatic aberrations due to the different wavelengths of the first light source and the target light source.

In accordance with yet a further feature of the one embodiment of the present invention, the first light source and/or the target light source can include a laser.

In a further embodiment, the microscope is provided with an optical fiber into which the illuminating light of the at least first light source and the light of the target light source can be coupled in order to achieve the collinearity of the illuminating light and the light of the target light source. In this case, the combining element can include a beam splitter. Alternatively, the combining element can include an AOTF, an AOBS or an AOM.

Further advantageous refinements of the invention can be found in the discussion below.

Figure 1:
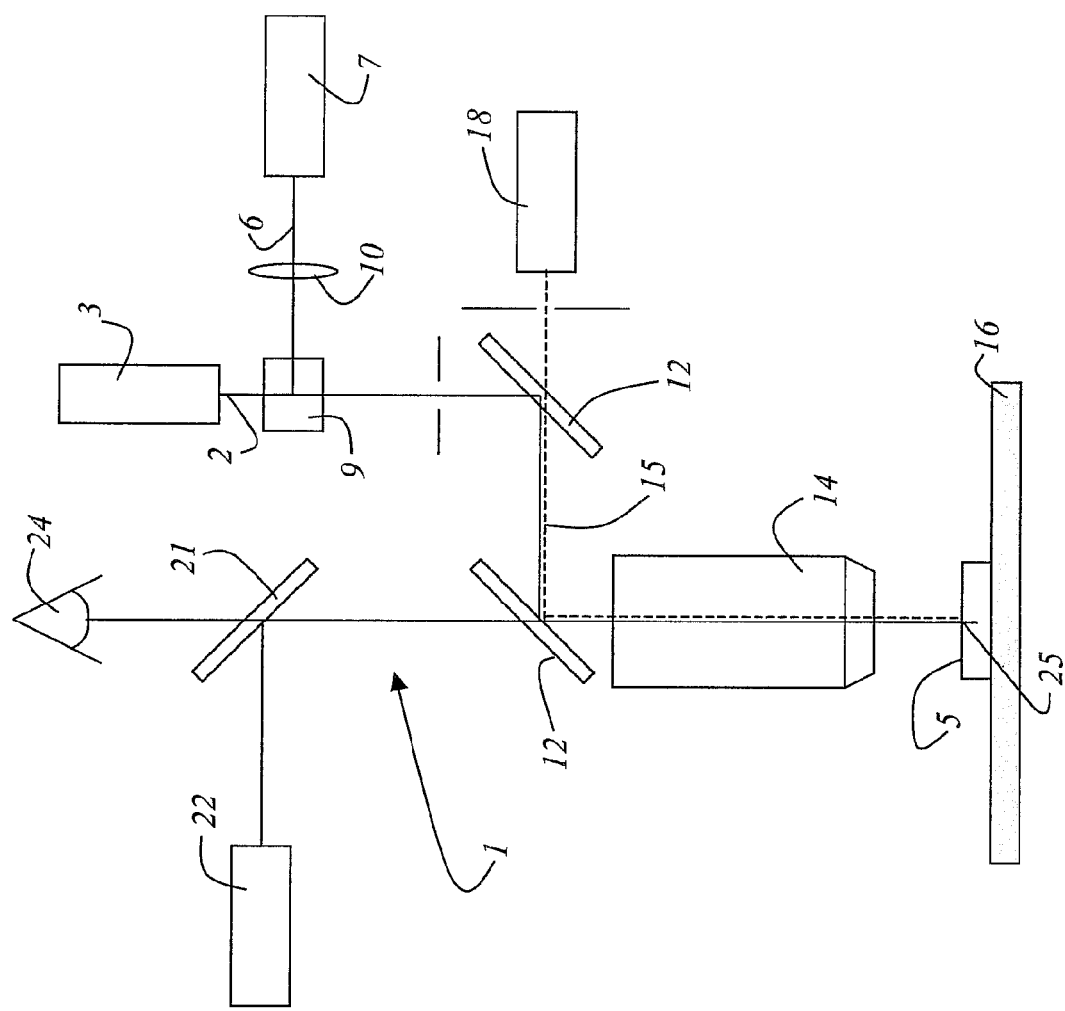
FIG. 1 shows a schematic illustration of a first embodiment of the invention.

FIG. 1 schematically describes a microscope system 1 for conducting FCS measurements. The microscope system 1 is provided with at least one first light source 3 which emits illuminating light which is directed onto a sample volume 5 or a sample. Additionally, a target light source 7 for marking the FCS volume 5 is provided. The target light source 7 emits light 6, which is also directed onto the FCS volume. The wavelength of the illuminating light 2 of the first light source 3 differs from the wavelength of the light 6 of the target light source 7. The light 2 from the illuminating light source 3 and the light 6 from the target light source 7 are combined by a combining element 9 to form a common, collinear beam path. In this case, the combining element 9 can be designed to include a beam splitter. Optionally, the combining element 9 can include an AOTF, an AOBS or an AOM. A correcting optics 10 is provided between the target light source 7 and the combining element 9, in order to compensate chromatic aberrations due to the different wavelengths of the light 2 of the first light source 3 and the light 6 of the target light source 7. The light 2 of the first light source 3 and the light 6 of the target light source 7 is directed onto the sample volume 5 or the volume via a plurality of optical elements 12 and a microscope optics 14. The sample volume 5 or sample is preferably provided at least on an X-Y table 16, in order thereby to change the sample volume with respect to the position of the illuminating light. The sample volume 5 is excited to fluoresce due to the illumination by the first light source 3, so that the sample volume 5 emits a detection light 15, which is also directed onto the detector 18 via the microscope optics 14 and the optical elements. The light 6 of the target light source 7 has a longer wavelength than the illuminating light 2 of the first light source 3. In a first embodiment, the light 2 of the target light source 3 has a wavelength lying in the region of red light. The location of the light 6 of the target light source 7 on the sample volume 5 can therefore be observed directly and visually by a user 24. If the light 6 of the target light source 7 lies in the wavelength region of IR light, a camera 22 is provided which produces an image for the user 24, so that the latter can recognize the location of the illuminating light 25 in the sample volume 5.

Figure 2:
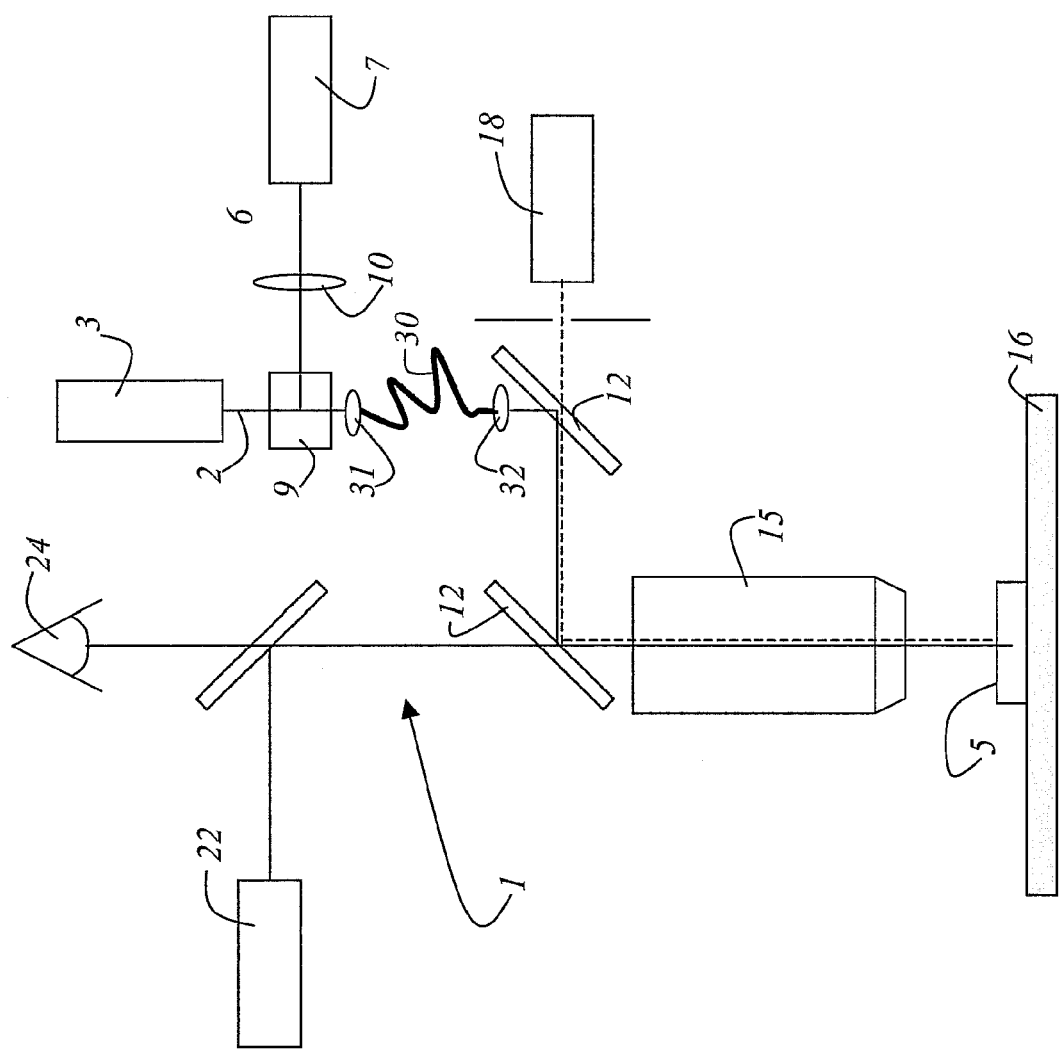
FIG. 2 shows a schematic illustration of a second embodiment of the invention.

FIG. 2 shows a further embodiment of the microscope system 1. Arranged downstream of the combining element 9 is an optical fiber 30 into which the illuminating light 2 of the at least first light source 3 and the light 6 of the target light source are coupled. The collinearity of the illuminating light is achieved by coupling the illuminating light 2 of the light 6 of the target light source 7 into the optical fiber 30. This ensures that the light 6 of the target light source 7 and the illuminating light 2 of the at least first light source 3 impinge on a shared impingement location 25 in the sample volume 5 or in the sample. The optical fiber 30 can be provided with a coupling-in optics 31 and a coupling-out optics 32.

What is claimed is:

1. A method of conducting fluorescence correlation spectroscopy measurements, the method comprising:
   providing a sample volume;
   emitting a target light having a first wavelength from a target light source;
   marking a fluorescence correlation spectroscopy volume in the sample volume with the target light by directing the target light onto the sample volume;
   emitting an illuminating light having a second wavelength from an illuminating light source, the second wavelength being different than the first wavelength;
   directing the illuminating light onto the sample volume; and
   recognizing a location of the illuminating light based on a location of the target light in the sample volume.

2. The method recited in claim 1, further comprising combining the target light with the illuminating light using a combining element so as to form a common beam path.

3. The method recited in claim 2, wherein the first wavelength is longer than the second wavelength.

4. The method recited in claim 3, further comprising compensating chromatic aberrations resulting from the difference in the first and second wavelengths using correcting optics.

5. The method recited in claim 4, further comprising coupling the target light and the illuminating light in an optical fiber downstream of the combining element.

6. The method recited in claim 2, further comprising coupling the target light and the illuminating light in an optical fiber downstream of the combining element.

7. The method recited in claim 1, wherein the first wavelength is longer than the second wavelength.

8. The method recited in claim 7, wherein the first wavelength is in a region of red light, and wherein the recognizing the location of the illuminating light in the sample volume is based on a visual observation of a location of the target light in the sample volume.

9. The method recited in claim 7, wherein the first wavelength is in a region of IR light, and wherein the recognizing the location of the illuminating light in the sample volume includes producing an image with a camera.

10. The method recited in claim 1, further comprising compensating chromatic aberrations resulting from the difference in the first and second wavelengths using correcting optics.

* * * * *